United States Patent
Amini

[19]

[11] Patent Number: 5,852,404
[45] Date of Patent: Dec. 22, 1998

[54] APPARATUS FOR THE DETECTION AND IDENTIFICATION OF METAL PARTICLES, COOLANT OR WATER IN ENGINE OIL OR HYDRAULIC FLUID

[76] Inventor: Bijan K. Amini, 5110 San Felipe #131, Houston, Tex. 77056

[21] Appl. No.: 688,395

[22] Filed: Jul. 30, 1996

[51] Int. Cl.⁶ .................................................... G08B 21/00
[52] U.S. Cl. ...................... 340/627; 340/631; 73/53.07; 324/698
[58] Field of Search ..................... 340/627, 631; 324/698, 700; 73/863.21, 53.07; 184/108; 62/129, 470

[56] References Cited

U.S. PATENT DOCUMENTS

| | | | |
|---|---|---|---|
| 2,552,088 | 5/1951 | Davis | 340/631 |
| 3,710,615 | 1/1973 | Johnson et al. | 340/627 |
| 4,598,280 | 7/1986 | Bradford | 340/631 |
| 4,629,334 | 12/1986 | Hochstein | 73/53.07 |
| 4,785,287 | 11/1988 | Honma et al. | 340/631 |
| 5,089,780 | 2/1992 | Megerle | 324/698 |
| 5,260,667 | 11/1993 | Garcia-Golding et al. | 324/698 |
| 5,264,832 | 11/1993 | Parmer | 340/631 |

*Primary Examiner*—Jeffery A. Hofsass
*Assistant Examiner*—John Tweel, Jr.
*Attorney, Agent, or Firm*—Alton W. Payne

[57] ABSTRACT

An apparatus for the detection and identification of metal particles, coolant or water in engine oil or hydraulic fluid. The apparatus comprising means for generating a high frequency oscillating field within the fluid, means for generating an electric field within the fluid, means for measuring the real and imaginary part of the complex impedance associated with the interaction of the electric field and the fluid, and means for determining at least one of the presence, the absence or the variation of metal particles, coolant or water in the fluid based upon the impedance measured. The high frequency oscillating field has a frequency range of approximately 2 megahertz to 10 gigahertz. Also, apparatus for the detection and characteristic identification of contaminants in engine oil or hydraulic fluid is provided. The apparatus for the characteristic identification of contaminants in engine oil or hydraulic fluid comprises means for generating a high frequency oscillating field within the fluid, means for generating an electric field within the fluid, means for measuring the real and imaginary part of the complex impedance associated with the interaction of the electric field and the fluid, identifying the real and complex parts of the complex impedance associated with the contaminants for providing a signature of the contaminants in the fluid, and means for determining at least one of the presence, the absence or the variation of metal particles, coolant or water in the fluid based upon the impedance measured.

3 Claims, 3 Drawing Sheets

5,852,404

APPARATUS FOR THE DETECTION AND IDENTIFICATION OF METAL PARTICLES, COOLANT OR WATER IN ENGINE OIL OR HYDRAULIC FLUID

FIELD OF THE INVENTION

The present invention relates generally to an apparatus for the detection and identification of metal particles, coolant or water in engine oil or hydraulic fluid. Specifically, the present invention relates to an apparatus and method that uses a capacitive microwave field.

BACKGROUND OF THE INVENTION

The presence of water or coolant in engine oil or in hydraulic fluid is very serious. In the engine, it is the indication of coolant manifold failure, and in hydraulic fluid, it foretells of damage to pistons and valves. The fact that water and coolant are incompressible liquids makes them ideal scouring and cutting media under high pressures. Therefore, the early detection of metal particles, coolant or water in engine oil or hydraulic fluid is very important to prevent damage to engine or hydraulic machinery. Additionally, loose metallic shavings from the engine or hydraulic parts are a first sign of serious internal problems.

Described herein is an apparatus which has been shown to be very effective in the detection and identification of coolant, water and metallic shavings in engine oil or hydraulic fluid.

SUMMARY OF THE INVENTION

To achieve the foregoing objects, features, and advantages and in accordance with the purpose of the invention as embodied and broadly described herein, an apparatus for the detection and identification of metal particles, coolant or water in engine oil or hydraulic fluid is provided. The apparatus comprising means for generating a high frequency oscillating field within the fluid, means for generating an electric field within the fluid, means for measuring the real and imaginary part of the complex impedance associated with the interaction of the electric field and the fluid, and means for determining at least one of the presence, the absence or the variation of metal particles, coolant or water in the fluid based upon the impedance measured. The high frequency oscillating field has a frequency range of approximately 2 megahertz to 10 gigahertz. Also, apparatus for the detection and characteristic identification of contaminants in engine oil or hydraulic fluid is provided. The apparatus for the characteristic identification of contaminants in engine oil or hydraulic fluid comprises means for generating a high frequency oscillating field within the fluid, means for generating an electric field within the fluid, means for measuring the real and imaginary part of the complex impedance associated with the interaction of the electric field and the fluid, identifying the real and complex parts of the complex impedance associated with the contaminants for providing a signature of the contaminants in the fluid, and means for determining at least one of the presence, the absence or the variation of metal particles, coolant or water in the fluid based upon the impedance measured.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

A capacitive microwave field apparatus, in several embodiments, is shown in FIG. 1. The commonality of these embodiments is that a very high frequency (2 megahertz to 10 gigahertz) oscillating field is put into a contained electric field such as that found in a capacitor. At such frequencies, the electric field is analogous to a radar that has a closely coupled transmitter and detector antennae. These antennae will measure the real and imaginary part of the complex impedance. The parts of the complex impedance are normally described as the transmissivity and loss tangent. Because the frequencies are so high, the capacitive value resistance is very low. Thus, the resistance of most contaminants found in hydraulic fluids or engine oils has a higher value and will therefore not cause a short circuit across the capacitive plates. The present invention shows that there can be as much as 30% by volume of water in engine oil and the device still is not fouled or shorted out. A second reason for such frequencies is to provide characteristic identification of the contaminants. It has been shown in the art that the real and complex parts of the complex impedance are different for every fluid. Such a phenomenon provides a signature that is unique over a frequency band from 1 megahertz to 10 gigahertz. Most fluids that are identified as low dielectrics show their unique signatures before 1 gigahertz. Therefore, by using microwave spectrometry, it is possible to identify the fluid and the containment very accurately. Since oil in the engine accumulates carbon and tars, it is also possible to detect when the engine oil needs to be changed.

Figure 1A:
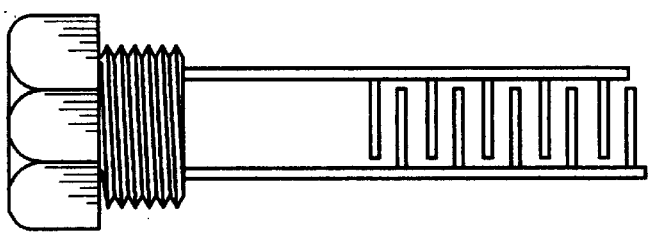
FIG. 1A is a perspective, cut-away view of a preferred embodiment of the present invention.
Figure 1B:
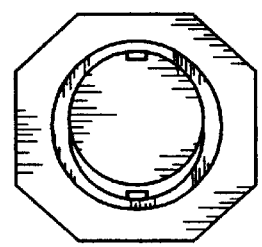
FIG. 1B is a cross-sectional view of a preferred embodiment of the present invention.
Figure 1C:
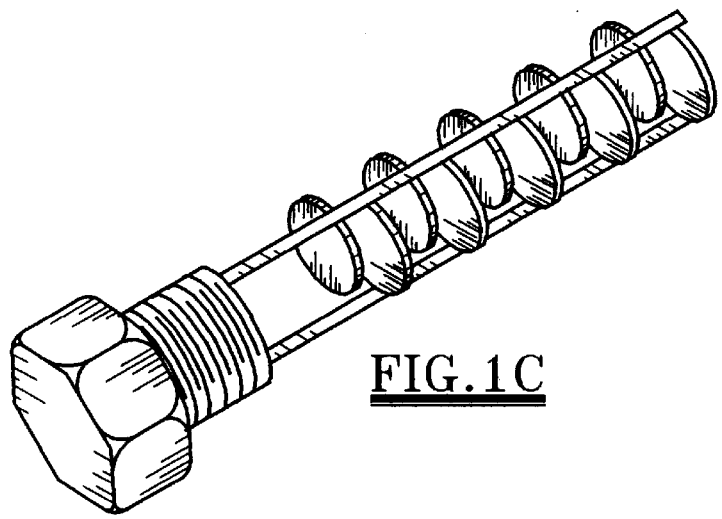
FIG. 1C is a perspective, cut-away view of a preferred embodiment of the present invention.
Figure 1D:
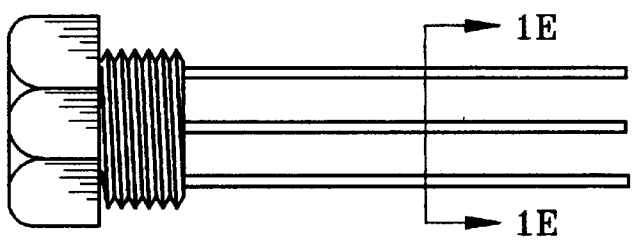
FIG. 1D is a perspective, cut-away view of another preferred embodiment of the present invention.
Figure 1E:
FIG. 1E is a schematic cross-sectional view of the preferred embodiment of the present invention illustrated in FIG. 1D.
Figure 1F:
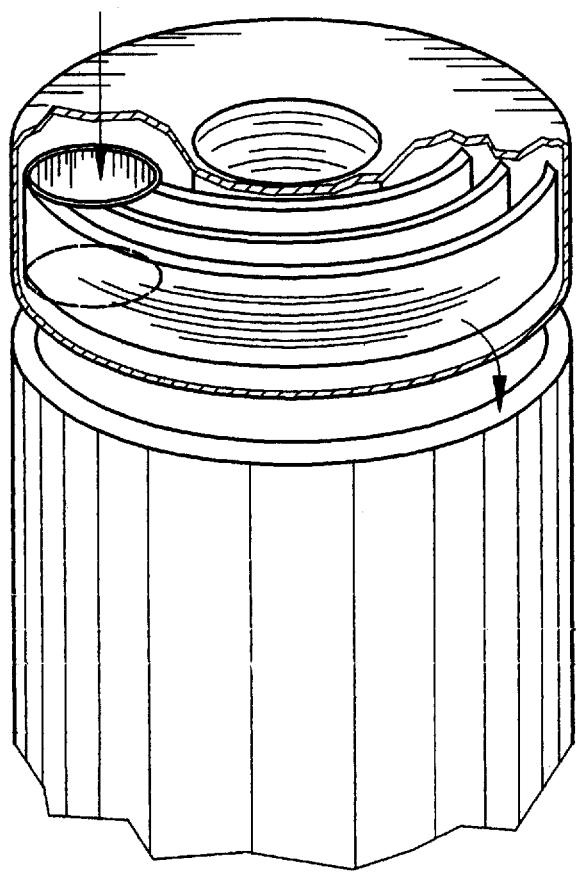
FIG. 1F is a perspective, cut-away view of another preferred embodiment of the present invention adapted for use with a filter device.
Figure 2:
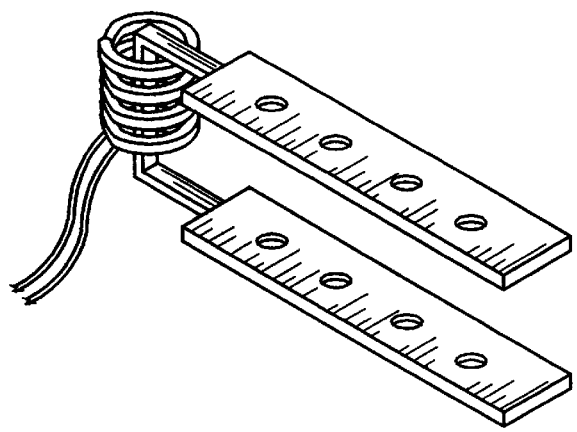
FIG. 2 is a schematic view of a preferred embodiment of the apparatus of the present invention illustrating the use of a solenoid and plates with drain holes.

The detection of loose metallic particles is accomplished by placing an electromagnetic field on the electric field by means of a solenoid as shown in FIG. 2. The apparatus of the present invention has a high sensitivity of detection of approximately 0.01% change of dielectric. Metallic particles as small as a pin head cause a voltage baseline displacement on the output. The particle is attached to one of the magnetized plates that are placed in the fluid. Coolant and water droplets on the other hand create transient spikes in an output voltage as they are carried past the electric field by the moving engine oil or hydraulic fluid. The metallic particles are then released when the solenoid field is turned off.

Figure 3A:
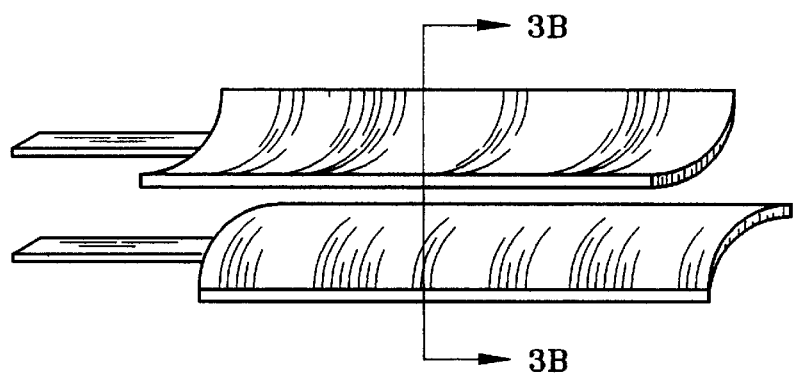
FIG. 3 is a schematic representation of the capacitive microwave fields edge effects created by turning out the edges of plates.
Figure 3B:
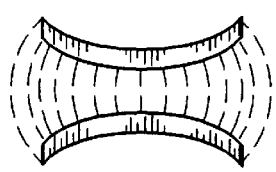

To make the apparatus more sensitive to the fluid movement, it is possible to counter intuitively increase the capacive microwave fields edge effects by turning out the edges. This is shown in FIG. 3. The electric filed lines always stay perpendicular to the metallic surface, therefore they bow out as shown. This makes the device more sensitive to edge effects which in this case is desirable for the detection of contaminates in the flow. This geometry also presents a larger opening access to the field for contaminant particulate or droplets.

Finally, the presence of this device in the oil pan or hydraulic reservoir becomes an excellent liquid level gauge that is resistant to false readings from fouling.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. An apparatus for the detection and identification of metal particles, coolant or water in engine oil or hydraulic fluid, the apparatus comprising:
   (a) means for generating a high frequency oscillating electric field within the fluid,
   (b) means for generating an electromagnetic field within the fluid,
   (c) means for measuring a real part and an imaginary part of the complex impedance associated with the interaction of the electric field and the fluid,
   (d) means for determining at least one of the presence, the absence or the variation of metal particles, coolant or water in the fluid based upon the real part and an imaginary part of the complex impedance measured.

2. An apparatus for the detection and identification of metal particles, coolant or water in engine oil or hydraulic fluid, as defined in claim 1 wherein the high frequency oscillating field has a frequency range of approximately 2 megahertz to 10 gigahertz.

3. An apparatus for the detection and characteristic identification of contaminants in engine oil or hydraulic fluid, the apparatus comprising:
   (a) means for generating a high frequency oscillating electric field within the fluid,
   (b) means for generating an electromagnetic field within the fluid,
   (c) means for measuring a real part and an imaginary part of the complex impedance associated with the interaction of the electric field and the fluid,
   (d) identifying the real and imaginary parts of the complex impedance associated with the contaminants for providing a signature of the contaminants in the fluid, and
   (e) means for determining at least one of the presence, the absence or the variation of metal particles, coolant or water in the fluid based upon the identified real and imaginary parts of the complex impedance measured.

* * * * *